(12) United States Patent
Chen et al.

(10) Patent No.: US 11,834,388 B2
(45) Date of Patent: Dec. 5, 2023

(54) CONTINUOUS-FLOW PREPARATION METHOD OF DICLOFENAC SODIUM

(71) Applicant: Fudan University, Shanghai (CN)

(72) Inventors: Fener Chen, Shanghai (CN); Dang Cheng, Shanghai (CN); Lulu Wang, Shanghai (CN); Ge Meng, Shanghai (CN); Yingtang Ning, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 18/172,865

(22) Filed: Feb. 22, 2023

(65) Prior Publication Data

US 2023/0192595 A1  Jun. 22, 2023

(30) Foreign Application Priority Data

Feb. 25, 2022  (CN) .......................... 202210178945.7

(51) Int. Cl.
  *C07C 227/18* (2006.01)
  *C07C 227/40* (2006.01)

(52) U.S. Cl.
  CPC .......... *C07C 227/18* (2013.01); *C07C 227/40* (2013.01)

(58) Field of Classification Search
  None
  See application file for complete search history.

(56) References Cited

U.S. PATENT DOCUMENTS

| 3,558,690 A | 1/1971 | Sallmann et al. |
| 4,978,773 A | 12/1990 | Grafe et al. |

FOREIGN PATENT DOCUMENTS

| CN | 1580039 A | 2/2005 |
| CN | 108947861 A | 12/2018 |
| DE | 1815802 A1 | 7/1969 |
| EP | 0380712 A1 | 8/1990 |
| GB | 1132128 A | 10/1968 |

(Continued)

OTHER PUBLICATIONS

Shengqian Fei et al., Synthesis of antipyretic, analgesic and anti-inflammatory drug diclofenac sodium, Chinese Journal of Pharmaceutical Industry, 1979, No. 11, pp. 14-19.

(Continued)

*Primary Examiner* — Sudhakar Katakam
*Assistant Examiner* — Jennifer C Sawyer

(57) ABSTRACT

This application relates to pharmaceutical engineering, and more particularly to a continuous-flow preparation method of diclofenac sodium. The continuous-flow preparation method includes: subjecting aniline and chloroacetic acid to amidation to obtain 2-chloro-N-phenylacetamide (3); subjecting 2-chloro-N-phenylacetamide (3) and 2,6-dichlorophenol to continuous condensation to obtain N-(2,6-dichlorophenyl)-2-hydroxy-N-phenylacetamide (5); subjecting N-(2,6-dichlorophenyl)-2-hydroxy-N-phenylacetamide (5) and thionyl chloride to chlorination to obtain N-(2,6-dichlorophenyl)-2-chloro-N-phenylacetamide (6); subjecting N-(2,6-dichlorophenyl)-2-chloro-N-phenylacetamide (6) to Friedel-Crafts alkylation in the presence of aluminum chloride to obtain 1-(2,6-dichlorophenyl)-1,3-dihydro-2H-indol-2-one (7); and subjecting 1-(2,6-dichlorophenyl)-1,3-dihydro-2H-indol-2-one (7) to hydrolysis to obtain the diclofenac sodium.

10 Claims, 1 Drawing Sheet

(56) References Cited

FOREIGN PATENT DOCUMENTS

NL        6604752 A    10/1966
WO     9222522 A1    12/1992

OTHER PUBLICATIONS

Fener Chen et al., Synthesis of Diclofenac Sodium By Rearrangement II ., Chinese Journal of Pharmaceuticals, 1998, No. 8, pp. 339-341.

Bingchang Qin et al., Study on the synthetic process of diclofenac, Applied Chemical Industry, 2008 No. 3 issue, pp. 275-278,297.

Unit A (amidation unit)
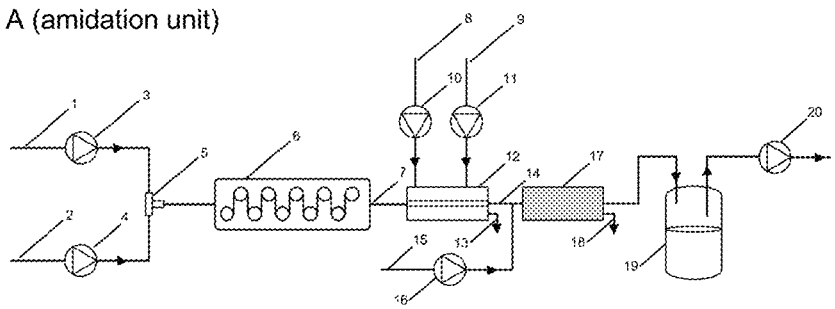
Unit B (condensation and Smiles rearrangement unit)
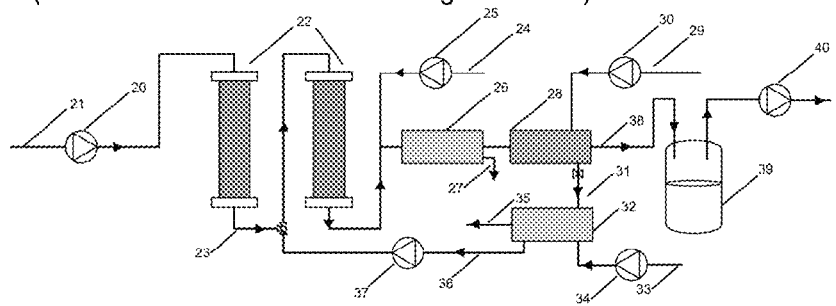
Unit C (chlorination unit)
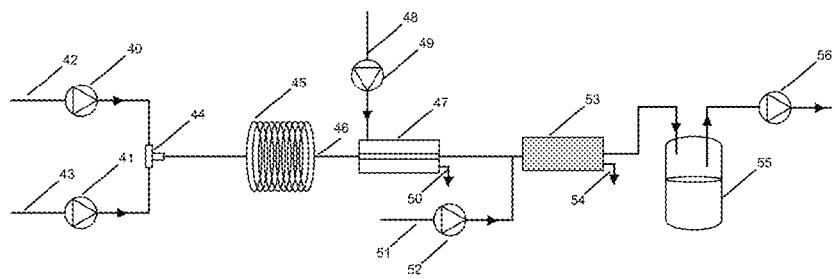
Unit D (Friedel-Crafts alkylation unit)
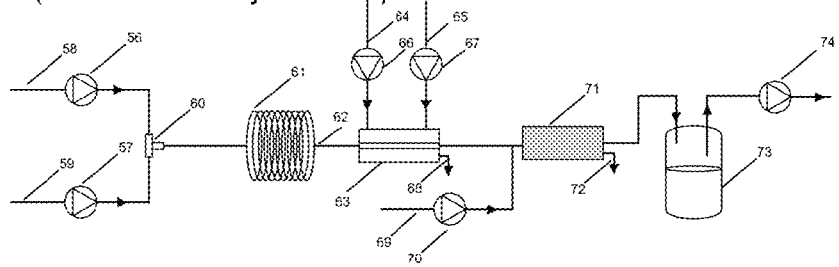
Unit E (hydrolysis unit)
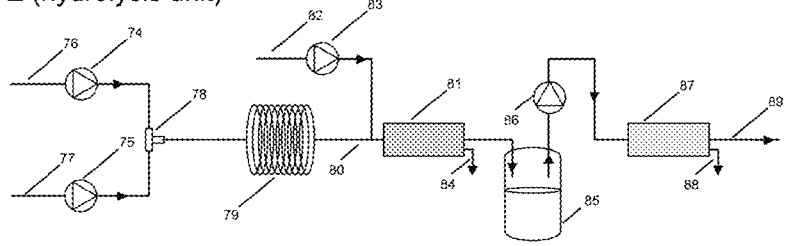

CONTINUOUS-FLOW PREPARATION METHOD OF DICLOFENAC SODIUM

CROSS-REFERENCE TO RELATED APPLICATIONS

This application claims the benefit of priority from Chinese Patent Application No. 202210178945.7, filed on Feb. 25, 2022. The content of the aforementioned application, including any intervening amendments thereto, is incorporated herein by reference in its entirety.

TECHNICAL FIELD

This application relates to pharmaceutical engineering, and more particularly to a continuous-flow preparation method of diclofenac sodium.

BACKGROUND

Diclofenac sodium, also known as diclofenac, is a non-steroidal anti-inflammatory analgesic derived from arylacetic acids, which has been developed by Ciba-Geigy Ltd. in Switzerland, and was launched in 1974. Clinically, the diclofenac sodium has antipyretic and analgesic effects, and is widely applied to treatments of various types of rheumatoid arthritis, lupus erythematosus, neuritis, cancer, postoperative pain and fever caused by various reasons. Diclofenac mainly works by inhibiting the synthesis of prostaglandins in vivo. Compared with other anti-inflammatory analgesics, the diclofenac sodium has stronger anti-inflammatory effect, for example, the anti-inflammatory effect of the diclofenac sodium is 2-2.5 times stronger than the anti-inflammatory effect of indomethacin, and 20-50 times stronger than the anti-inflammatory effect of aspirin. In addition, the diclofenac sodium is absorbed rapidly with oral administration, and excreted from the body fast, such that it has no accumulation effect during long-term administration. The individual differences of the diclofenac sodium are small. As a result, the diclofenac sodium is ahead in anti-rheumatic drugs and has been widely applied. The structure of diclofenac sodium is shown in the following formula (1):

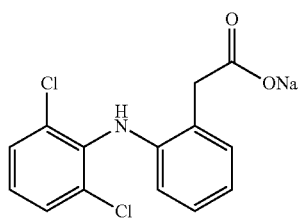

(1)

U.S. Patent Publication No. 3558690, British Patent Publication No. 1132128 and Fei Shengqian et al. (Pharmaceutical Industry, 1979, 10, 14) disclosed a method for preparing diclofenac sodium (1) by subjecting a raw material o-chlorobenzoic acid to Ullmann condensation and decarboxylation to obtain a key intermediate 2,6-dichloroaniline followed by acylation, cyclization, hydrolysis reaction for ring opening and salt formation. This method has easy-to-obtain raw materials, such that it is the earliest synthetic route for preparing diclofenac sodium in China. However, this method struggles with the lengthy steps, strong toxicity and high corrosion of the compound used in the synthesis, severe environmental pollution and poor conversion rate.

Netherlands Patent Application No. 6604752, and Japanese Patent Publication No. 23418 disclosed 2,6-dichlorodiphenylamine is prepared in one step by subjecting bromobenzene and 2,6-dichloroaniline to Ullmann condensation, and the yield of the 2,6-dichlorodiphenylamine is close to 50%. This method was once adopted by many factories. However, some by-products such as N-phenyl-2-chloro-6-bromoaniline that are difficult to separate will occur in the synthesis route. These aromatic bromides can cause gastric ulcer, or other side effects, and thus the industrial application of this method is significantly limited.

German Patent Publication No. 1815802 disclosed that the oxalyl chloride is used as the acylating reagent to obtain the intermediate N-arylindole-2,3-dione by means of the Stoll synthesis method, and then the intermediate is subjected to reduction and hydrolysis reaction to obtain the diclofenac sodium. Although the yield of the diclofenac sodium is high, this method uses the oxalyl chloride which is expensive, highly toxic, highly corrosive and irritating, leading to serious three-waste (waste gas, waste water and industrial residue) pollution, such that the labor protection requirements are high, and the synthesis steps are lengthy.

Japanese patent disclosed a method for preparing diclofenac sodium, where o-chlorobenzoic acid and 2,6-dichloroaniline are subjected to condensation, and then the diazomethane or sodium cyanide the is taken as the carbon source to obtain the diclofenac sodium. This method adopts the explosive diazomethane or highly toxic sodium cyanide, which is dangerous in operation and causes serious environmental pollution, limiting the industrial production.

EP No. 0380712 and WO No. 022522 disclosed a method for preparing the diclofenac sodium, which is performed by subjecting the raw material aniline to acylation, etherification and Chapman rearrangement. Chen Fener et al. has significantly improved this method. Chen Fener (Chinese Journal of Pharmaceutical Industry, 1998, 29, 339), US Patent Publication No. 4978773 and Qin Bingchang et al. (Qin Bingchang, Chen Jing et al. Study on the synthetic process of diclofenac sodium [J]. Applied Chemical Industry, 2008,37(3):275-278297.) disclosed a method for preparing diclofenac sodium performed by subjecting the 2,6-dichlorodiphenylamine and the chloroacetyl chloride to acylation, intramolecular Friedel-Crafts alkylation reaction and hydrolysis reaction for ring opening. This method is one of the main routes for producing the diclofenac sodium in China, but has lengthy reaction steps, poor atom economy and serious three-waste pollution.

Chinese Patent Publication No. 1580039A disclosed a method for preparing diclofenac sodium performed by subjecting the raw material cyclohexanone to chlorination, carboxylation, hydrogenation and reduction, condensation, aromatization, salt formation, etc. Even though the yield of the diclofenac sodium is high, this method still uses highly toxic, corrosive and irritating materials such as chlorine gas, chloroacetyl chloride, organophosphorus, etc., leading to severe three-waste pollution, such that the labor protection requirements are high, and the synthesis steps are lengthy.

Chinese Patent Publication No. 108947861A disclosed a method for preparing the diclofenac sodium performed by subjecting the raw material phenylacetic acid to nitration, reduction, amidation, condensation, rearrangement, and hydrolysis reaction. This method has lengthy steps, and uses the corrosive and irritating nitration reagents and the relatively expensive palladium catalyst, which is not suitable for industrial production.

The above-mentioned methods for preparing diclofenac sodium are all carried out in the conventional batch reactor, which struggles with large time consumption, low yield, complicated operation, high labor intensity and serious potential safety hazard.

SUMMARY

An objective of this application is to provide a continuous-flow preparation method of diclofenac sodium, which significantly shortens the reaction time, enhances the yield of the diclofenac sodium, improves the automation level and efficiency, notably reduces the energy consumption and improves the operation safety, facilitating the industrial application.

Technical solutions of this application are described as follows.

This application provides a method for preparing diclofenac sodium using a continuous-flow reaction system, wherein the continuous-flow reaction system comprises a first unit, a second unit, a third unit, a fourth unit and a fifth unit successively connected in series; the first unit comprises a first mixer, a first microchannel reactor and a first storage tank connected in sequence; the second unit comprises a second mixer, a second microchannel reactor, a third microchannel reactor, a filter and a second storage tank; the third unit comprises a third mixer, a fourth microchannel reactor and a third storage tank connected in sequence; the fourth unit comprises a fourth mixer, a fifth microchannel reactor, and a fourth storage tank connected in sequence; the fifth unit comprises a fifth mixer and a sixth microchannel reactor; and the method comprises:

(S1) respectively feeding a mixed solution of chloroacetic acid and a first catalyst, and an organic solution of aniline to the first mixer for mixing to obtain a first mixture; and allowing the first mixture to flow out of the first mixer and enter the first microchannel reactor for amidation reaction;

(S2) subjecting a reaction mixture flowing out of the first microchannel reactor to continuous quenching, liquid-liquid extraction and separation to collect an organic phase;

(S3) concentrating the organic phase obtained in step (S2) to obtain 2-chloro-N-phenylacetamide (3) followed by dissolving with a first organic solvent to obtain a 2-chloro-N-phenylacetamide (3) solution; and transporting the 2-chloro-N-phenylacetamide (3) solution to the first storage tank;

(S4) respectively transporting the 2-chloro-N-phenylacetamide (3) solution in the first storage tank, and a mixed solution of 2,6-dichlorophenol and a phase transfer catalyst to the second mixer to for mixing to obtain a second mixture; and allowing the second mixture to flow out of the second mixer and enter the second microchannel reactor and the third microchannel reactor in sequence for continuous condensation and Smiles rearrangement; wherein the second microchannel reactor and the third microchannel reactor are both filled with a basic catalyst;

(S5) concentrating a reaction mixture flowing out of the third microchannel reactor followed by dissolving with a second organic solvent obtain a suspension; and transporting the suspension to the filter for filtration to collect a filtrate and a filter cake; wherein the filter cake is N-(2,6-dichlorophenyl)-2-hydroxyl-N-phenylacetamide (5);

(S6) concentrating the filtrate followed by dissolution with a third organic solvent and transportation to the third microchannel reactor for Smiles rearrangement to allow 2-(2,6 dichlorophenoxy)-N-phenylacetamide (4) in the filtrate to be converted into N-(2,6-dichlorophenyl)-2-hydroxyl-N-phenylacetamide (5); and repeating step (S5) to obtain another filter cake;

(S7) combining filter cakes followed by dissolving with a fourth organic solvent to obtain a N-(2,6-dichlorophenyl)-2-hydroxyl-N-phenylacetamide (5) solution; and transporting the N-(2,6-dichlorophenyl)-2-hydroxyl-N-phenylacetamide (5) solution to the second storage tank;

(S8) respectively transporting the N-(2,6-dichlorophenyl)-2-hydroxyl-N-phenylacetamide (5) solution in the second storage tank and a mixed solution of thionyl chloride and a second catalyst to the third mixer for mixing to obtain a third mixture; allowing the third mixture to flow out of the third mixer and enter the fourth microchannel reactor for chlorination;

(S9) subjecting a reaction mixture flowing out from the fourth microchannel reactor to continuous quenching, liquid-liquid extraction and separation to collect an organic phase;

(S10) concentrating the organic phase obtained in step (S9) followed by dissolution with a fifth organic solvent to obtain a N-(2,6-dichlorophenyl)-2-chloro-N-phenylacetamide (6) solution; transporting the N-(2,6-dichlorophenyl)-2-chloro-N-phenylacetamide (6) solution to the third storage tank;

(S11) respectively transporting the N-(2,6-dichlorophenyl)-2-chloro-N-phenylacetamide (6) solution and an organic solution of aluminum chloride to the fourth mixer for mixing and preheating to obtain a fourth mixture; allowing the fourth mixture to flow out of the fourth mixer and enter the fifth microchannel reactor for Friedel-Crafts alkylation (S12) subjecting a reaction mixture flowing out of the fifth microchannel reactor to continuous quenching, liquid-liquid extraction and separation to collect an organic phase;

(S13) concentrating the organic phase obtained in step (S12) followed by dissolving with a sixth organic solvent to obtain a 1-(2,6-dichlorophenyl)-1,3-dihydro-2H-indol-2-one (7) solution; transporting the 1-(2,6-dichlorophenyl)-1,3-dihydro-2H-indol-2-one (7) solution to the fourth storage tank;

(S14) respectively transporting the 1-(2,6-dichlorophenyl)-1,3-dihydro-2H-indol-2-one (7) solution in the fourth storage tank and a solution of an inorganic base to the fifth mixer for mixing to obtain a fifth mixture; and allowing the fifth mixture to flow out of the fifth mixer and enter the sixth microchannel reactor for hydrolysis reaction to obtain the diclofenac sodium (1); as shown in the following reaction scheme:

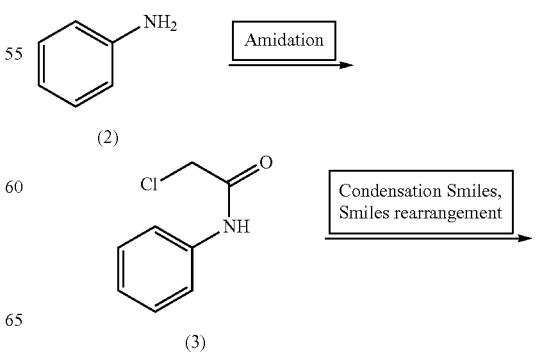

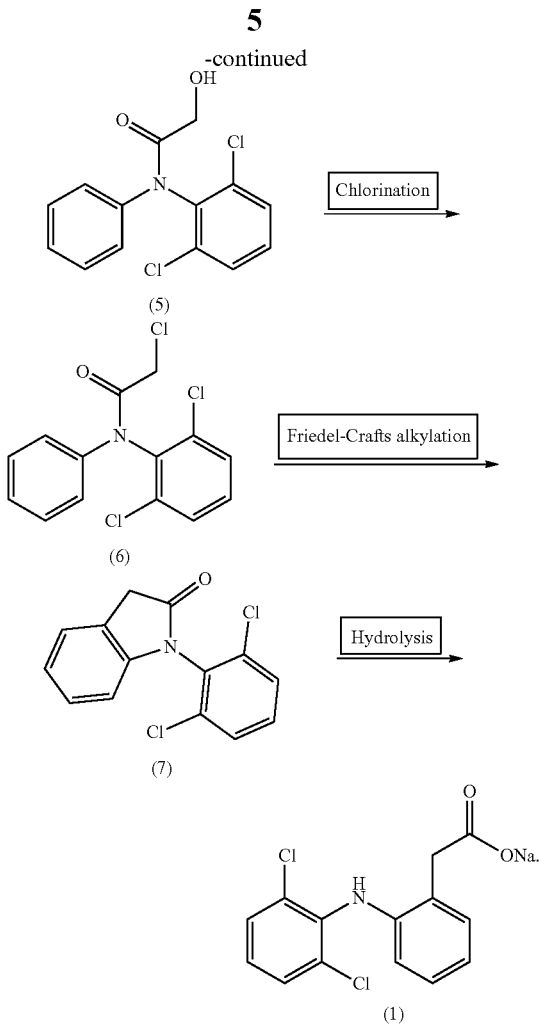

In an embodiment, in step (S1), the first catalyst is a boronic acid catalyst. Preferably, the first catalyst is selected from the group consisting of o-halogenated arylboronic acid, aminoboronic acid, boric acid and boronate ester.

In an embodiment, in step (S1), a molar ratio of the aniline to the chloroacetic acid to the first catalyst is 1:(1-5):(0.001-0.5).

In an embodiment, the amidation reaction is performed in an organic solvent selected from the group consisting of toluene, xylene, mesitylene, chlorobenzene, dichlorobenzene, N,N-dimethylacetamide ethyl acetate and acetonitrile.

In an embodiment, the first microchannel reactor is controlled at 70~170° C., and a residence time of the reaction mixture in the first microchannel reactor is 5~100 min.

In an embodiment, in step (S2), the reaction mixture flowing out from the first microchannel reactor is subjected to quenching with an aqueous solution of an inorganic base, liquid-liquid extraction with a non-polar organic solvent, and separation to collect the organic phase; the aqueous solution of the inorganic base contains 1-50% by weight of the inorganic base; the inorganic base is selected from the group consisting of sodium carbonate, potassium carbonate, sodium bicarbonate, potassium bicarbonate, sodium hydroxide and potassium hydroxide; a pH of the reaction mixture after quenched is 6-8; the non-polar organic solvent is an acetate solvent, a substituted benzene solvent or a halogenated hydrocarbon solvent; the liquid-liquid extraction is performed at 10-60° C.; the continuous quenching, liquid-liquid extraction and separation are performed in a first liquid-liquid extraction separator; a residence time of the reaction mixture in the first liquid-liquid extraction separator is 0.1-20 min.

In an embodiment, in step (S3), the first organic solvent is selected from the group consisting of toluene, xylene, acetonitrile, N,N-dimethylformamide, ethyl acetate, acetone and n-butanol.

In an embodiment, in step (S4), the phase transfer catalyst is selected from the group consisting of polyethylene glycol 400 (PEG-400), polyethylene glycol 600 (PEG-600), benzyltriethylammonium chloride and tetrabutylammonium bromide; a molar ratio of the 2-chloro-N-phenylacetamide (3) to the 2,6-dichlorophenol to the phase transfer catalyst is 1:(0.5-2):(1-5); the basic catalyst is an inorganic base or an organic base. Preferably, the inorganic base is selected from the group consisting of sodium hydroxide, calcium hydroxide, sodium carbonate, sodium bicarbonate, potassium carbonate, potassium bicarbonate and sodium hydrogen; and the organic base is selected from the group consisting of a polymer-supported 1,8-diazabicyclo [5.4.0]undec-7-ene (DBU) and a polymer-supported 1,5,7-triazabicyclo[4.4.0]dec-5-ene (TBD).

In an embodiment, in step (S4), the second microchannel reactor is controlled at 50-160° C., and the third microchannel reactor is controlled at 0-100° C.; a residence time of the reaction mixture in the second microchannel reactor is 1-120 min, and a residence time of the reaction mixture in the third microchannel reactor is 0.5-40 min; and a back pressure of the third microchannel reactor is 0.1-5 MPa.

In an embodiment, in step (S5), the second organic solvent is a straight-chain alkane solvent, a substituted benzene solvent, an alkyl ether solvent or a cycloalkane solvent; the dissolution is performed at 0-60° C.; and a residence time of the suspension in the filter is 0.1-30 min. Preferably, the organic solvent is the straight-chain alkane solvent or the cycloalkane solvent.

In an embodiment, in step (S6), the third organic solvent is selected from the group consisting of toluene, xylene, acetonitrile, N,N-dimethylformamide, ethyl acetate, acetone and n-butanol.

In an embodiment, in step (S7), the fourth organic solvent is selected from the group consisting of N,N-dimethylformamide, dimethyl sulfoxide, thionyl chloride, toluene, acetonitrile, dichloromethane, 1,2-dichloroethane and ethyl acetate.

In an embodiment, in step (S8), the second catalyst is an organic base catalyst. Preferably, the second catalyst is selected from the group consisting of pyridine, N,N-dimethylaniline, triethylamine and N,N-dimethylformamide.

In an embodiment, in step (S8), a molar ratio of the N-(2,6-dichlorophenyl)-2-hydroxyl-N-phenylacetamide to thionyl chloride to the second catalyst is controlled to be 1:(1-4):(0.001-0.5).

In an embodiment, in step (S8), the fourth microchannel reactor is controlled at 20~100° C., and a residence time of the reaction mixture in the fourth microchannel reactor is 10~60 min.

In an embodiment, in step (S9), the reaction mixture flowing out from the fourth microchannel reactor is subjected to quenching with an aqueous solution of an inorganic base, liquid-liquid extraction with a non-polar organic solvent and separation to collect the organic phase; the aqueous solution of the inorganic base contains 1-50% by weight of the inorganic base; the inorganic base is selected from the group consisting of sodium carbonate, potassium carbonate, sodium bicarbonate, potassium bicarbonate, sodium hydroxide and potassium hydroxide; a pH of the reaction mixture after quenched is 6-8; the non-polar organic solvent is an acetate solvent, a substituted benzene solvent or a halogenated hydrocarbon solvent; the liquid-liquid extraction is performed at 10-60° C.; the continuous quenching, liquid-liquid extraction and separation are performed in a second liquid-liquid extraction separator; a residence time of the reaction mixture in the second liquid-liquid extraction separator is 0.1~20 min.

In an embodiment, in step (S10), the fifth organic solvent is selected from the group consisting of dichloromethane, 1,2-dichloroethane, chlorobenzene, toluene, xylene, dichlorobenzene, n-butanol and diphenyl ether.

In an embodiment, in step (S11), a molar ratio of the N-(2,6-dichlorophenyl)-2-chloro-N-phenylacetamide (6) to the aluminum chloride is controlled to be 1:(0.5-5); the fourth mixer is controlled at 10-100° C., and the fifth microchannel reactor is controlled to be 50-200° C.; and a residence time of the reaction mixture in the fifth microchannel reactor is 0.1~40 min.

In an embodiment, in step (S12), the reaction mixture flowing out of the fifth microchannel reactor is subjected to the quenching with an aqueous solution of an inorganic base, liquid-liquid extraction with a non-polar organic solvent and separation to collect the organic phase; the aqueous solution of the inorganic base contains 1~50% by weight of the inorganic base; the inorganic base is selected from the group consisting of sodium carbonate, potassium carbonate, sodium bicarbonate, potassium bicarbonate, sodium hydroxide and potassium hydroxide; a pH of the reaction mixture after quenched is 6-8; the non-polar organic solvent is an acetate solvent, a substituted benzene solvent or a halogenated hydrocarbon solvent; the liquid-liquid extraction is performed at 10-60° C.; the continuous quenching, liquid-liquid extraction and separation are performed in a third liquid-liquid extraction separator; and a residence time of the reaction mixture in the third liquid-liquid extraction separator is 0.1~20 min.

In an embodiment, in step (S13), the sixth organic solvent is selected from the group consisting of toluene, xylene, diphenyl ether, methanol and ethanol.

In an embodiment, in step (S14), the solution of the inorganic base contains 5-50% by weight of the inorganic base, and the inorganic base is selected from the group consisting of sodium carbonate, potassium carbonate, sodium bicarbonate and sodium hydroxide.

In an embodiment, in step (S14), the sixth microchannel reactor is controlled at 10-130° C., and a residence time of the reaction mixture in the sixth microchannel reactor is 1-60 min.

In an embodiment, the first mixer, the second mixer, the third mixer, the fourth mixer and the fifth mixer are each independently selected from the group consisting of static mixer, T-type micromixer, Y-type micromixer, cross-type mixer, coaxial flow micromixer and flow-focusing micromixer.

In an embodiment, the first microchannel reactor is a tubular microchannel reactor or a plate-type microchannel reactor; wherein the tubular microchannel reactor has an inner diameter of 100 μm~50 mm; the plate-type microchannel reactor comprises a first heat exchange layer, a reaction layer and a second heat exchange layer arranged in sequence from top to bottom; the reaction layer is provided with a reaction fluid channel; a hydraulic diameter of the reaction fluid channel is 100 μm-50 mm; and the first microchannel reactor is an agitated microchannel reactor.

In an embodiment, the first microchannel reactor is the agitated microchannel reactor. Preferably, the agitated microchannel reactor is a Coflore agitated cell reactor developed by AM technology limited company (UK).

In an embodiment, the second microchannel reactor and the third microchannel reactor are respectively a fixed-bed reactor; the fixed-bed reactor has an inner diameter of 100 μm~20 cm, and a length of 2~50 cm; and one or more fixed bed micro reactors are connected in series to form an operation unit.

In an embodiment, the fourth microchannel reactor, the fifth microchannel reactor and the sixed microchannel reactor are each independently a tubular microchannel reactor or a plate-type microchannel reactor; wherein the tubular microchannel reactor has an inner diameter of 100 μm-50 mm; the plate-type microchannel reactor comprises a first heat exchange layer, a reaction layer and a second heat exchange layer arranged in sequence from top to bottom; the reaction layer is provided with a reaction fluid channel; and a hydraulic diameter of the reaction fluid channel of the plate-type microchannel reactor is 100 μm-50 mm.

In an embodiment, the first liquid-liquid extraction separator, the second liquid-liquid extraction separator, and the third liquid-liquid extraction separator are each independently a plate-type microchannel extraction separator, a membrane extraction separator, or an annular centrifugal extraction separator; wherein the plate-type microchannel extraction separator has an inner diameter of 100 μm-10 mm; and comprises a mixing layer and a separation layer; the membrane extraction separator has a hydrophobic membrane with a pore size of 0.1~4 μm; the annular centrifugal extraction separator has a diameter of 10 cm~1 m; and one or more annular centrifugal extraction separators are connected in series to form an extraction-separation unit.

In an embodiment, the unit A (amidation unit) comprises a first feed pump, a second feed pump, a third feed pump, a fourth feed pump, a fifth feed pump, a first mixer, a first microchannel reactor, a first back pressure valve, a first liquid-liquid extraction separator, a first concentration device and a first storage tank; a first inlet of the first mixer is connected to the first feed pump for feeding of the aniline solution, and a second inlet of the first mixer is connected to the second feed pump for feeding of the mixed solution of chloroacetic acid and the first catalyst; an outlet of the first mixer is connected to an inlet of the first microchannel reactor; an outlet of the first microchannel reactor is connected to an inlet of the first back pressure valve; an outlet of the first back pressure valve is connected to a first inlet of the first liquid-liquid extraction separator; a second inlet of the first liquid-liquid extraction separator is connected to the third pump for feeding of the aqueous solution of the inorganic base, and a third inlet of the first liquid-liquid extraction separator is connected to the fourth pump for feeding of an organic solvent; a water-phase outlet of the first liquid-liquid extraction separator is connected to a water phase collecting device, and an organic-phase outlet of the first liquid-liquid extraction separator is connected to an inlet of the first concentration device; another controllable inlet of the first concentration device is connected to the fifth feed pump of another organic solvent; an outlet of the first concentration device is connected to an inlet of the first storage tank; and an outlet of the first storage tank is connected to an inlet of a sixth feed pump in the next unit for feeding of 2-chloro-N-phenylacetamide (3).

In an embodiment, the unit B (condensation and Smiles rearrangement unit) comprises the sixth feed pump, a seventh feed pump, an eighth feed pump, a ninth feed pump, a tenth feed pump a second mixer, a second microchannel reactor, a third microchannel reactor, a second back pressure valve, a second concentration device, a third concentration device, a filter device and a second storage tank; an inlet of the second microchannel reactor is connected to the sixth feed pump for feeding of 2-chloro-N-phenylacetamide (3), and an outlet of the second microchannel reactor is connected to an inlet of the third microchannel reactor; another controllable inlet of the third microchannel reactor is connected to an outlet of the second concentration device for concentrating in step (S6), and an outlet of the third microchannel reactor is connected to the second back pressure valve; an outlet of the second back pressure valve is connected to a first inlet of the third concentration device for concentrating in step (S7); a second inlet of the third concentration device is connected to the seventh feed pump of an organic solvent, and an outlet of the third concentration device is connected to a first inlet of the filter device; a second inlet of the filter device is connected to the eighth feed pump of another organic solvent; a first outlet of the filter device is connected to a first inlet of the second concentration device, and a second outlet of the filter device is connected to an inlet of the second storage tank (that is, the storage tank storing the N-(2,6-dichlorophenyl)-2-hydroxyl-N-phenylacetamide (5) solution); an outlet of the second storage tank is connected to an inlet of the ninth feed pump in the next unit for feeding of N-(2,6-dichlorophenyl)-2-hydroxyl-N-phenylacetamide (5); a second inlet of the second concentration device is connected to the tenth feed pump of an organic solvent; the outlet of the second concentration device is connected to a controllable inlet of the third microchannel reactor (unreacted N-(2,6-dichlorophenyl)-2-hydroxyl-N-phenylacetamide is reacted again form a cycle).

In an embodiment, the unit C (chlorination unit) comprises the ninth feed pump, an eleventh feed pump, a twelfth feed pump, a thirteenth feed pump, a third mixer, a second liquid-liquid extraction separator, a fourth concentration device, a third back pressure valve and a third storage tank; a first inlet of the third mixer is connected to the ninth feed pump for feeding of N-(2,6-dichlorophenyl)-2-hydroxyl-N-phenylacetamide (5), a second inlet of the third mixer is connected to the eleventh feed pump of the mixed solution of thionyl chloride and the second catalyst, and an outlet of the third mixer is connected to an inlet of the fourth microchannel reactor, and an outlet of the fourth microchannel reactor is connected to an inlet of the third back pressure valve; an outlet of the third back pressure valve is connected to a first inlet of the second liquid-liquid extraction separator, and a second inlet of the second liquid-liquid extraction separator is connected to the twelfth feed pump for feeding of water; a water-phase outlet of the second liquid-liquid extraction separator is connected to a water phase collecting device, an organic-phase outlet of the second liquid-liquid extraction separator is connected to a first inlet of the fourth concentration device; a second inlet of the fourth concentration device is connected to the thirteenth feed pump for feeding of an organic solvent, and an outlet of the fourth concentration device is connected to an inlet of the third storage tank (that is, the storage tank storing the N-(2,6-dichlorophenyl)-2-chloro-N-phenylacetamide (6) solution), and an outlet of the third storage tank is connected to an inlet of a fourteenth feed pump in the next unit for feeding of N-(2,6-dichlorophenyl)-2-chloro-N-phenylacetamide solution.

In an embodiment, the unit D (Friedel-Crafts alkylation unit) comprises the fourteenth feed pump, a fifteenth feed pump, a sixteenth feed pump, a seventeenth feed pump, an eighteenth feed pump, a fourth mixer, a fifth microchannel reactor, a third liquid-liquid extraction separator, a fifth concentration device, a fourth back pressure valve and a fourth storage tank. A first inlet of the fourth mixer used in step (S11) is connected to the fourteenth feed pump of the N-(2,6-dichlorophenyl)-2-chloro-N-phenylacetamide solution in the third storage tank, a second inlet of the fourth mixer is connected to the fifteenth feed pump for feeding of the organic solution of aluminum trichloride, and an outlet of the fourth mixer is connected to an inlet of the fifth microchannel reactor; an inlet of the fourth mixer is connected to an inlet of the fifth microchannel reactor; an outlet of the fifth microchannel reactor is connected to an inlet of the fourth back pressure valve; an outlet of the fourth back pressure valve is connected to a first inlet of the third liquid-liquid extraction separator, and a second inlet of the third liquid-liquid extraction separator is connected to the sixteenth feed pump of an aqueous solution of an inorganic base, and a third inlet of the third liquid-liquid extraction separator is connected to the seventeenth feed pump of an organic solvent; a water-phase outlet of the third liquid-liquid extraction separator is connected to a water phase collecting device, and an organic-phase outlet of the third liquid-liquid extraction separator is connected to a first inlet of the fifth concentration device for concentrating in step (S13), and a second inlet of the fifth concentration device is connected to the eighteenth feed pump for feeding of an organic solvent; an outlet of the fifth concentration device is connected to an inlet of the fourth storage tank (that is, the storage tank storing the 1-(2,6-dichlorophenyl)-1,3-dihydro-2H-indol-2-one (7) solution), and an outlet of the fourth storage tank is connected to an inlet of a nineteenth feed pump in the next unit for feeding of 1-(2,6-dichlorophenyl)-1,3-dihydro-2H-indol-2-one (7) solution.

In an embodiment, the unit E (hydrolysis unit) comprises the nineteenth feed pump, a twentieth feed pump, a fifth mixer, a sixth microchannel reactor, a sixth concentration device and a fifth back pressure valve; a first inlet of the fifth mixer is connected to an outlet of the nineteenth feed pump of 1-(2,6-dichlorophenyl)-1,3-dihydro-2H-indol-2-one (7) solution, a second inlet of the fifth mixer is connected to the twentieth feed pump of an inorganic base solution, an outlet of the fifth mixer is connected to an inlet of the sixth microchannel reactor; an outlet of the sixth microchannel reactor is connected to the fifth back pressure valve; the reaction liquid flowing from the fifth back pressure valve is collected and subjected to simple post-processing to obtain the target product diclofenac sodium.

Compared with the prior art, this application has the following beneficial effects.

Compared with the existing synthetic methods using a traditional batch reactor, the continuous-flow preparation method provided herein has the following advantages.

1. By means of the excellent mass transfer, heat transfer and molecular mixing characteristics of the microchannel reactor, individual synthesis steps are significantly enhanced, and the reaction time of a single reaction is greatly shortened from more than ten hours (required by the traditional batch reactor) to tens of minutes or a few minutes. Moreover, the conversion rate and yield of each reaction are greatly improved.

2. By means of the microchannel reactor adopted herein, the hydrolysis side reaction of the Smiles rearrangement is maximally suppressed, such that the yield of the N-(2,6- dichlorophenyl)-2-hydroxyl-N-phenylacetamide (5) is improved from 77% (obtained by the traditional batch reactor) to more than 88%.

3. Regarding the continuous-flow preparation process based on the microchannel reactor, it is not required to separate the catalyst from the reaction mixture, so that the reaction system can run continuously for a long time, improving the process efficiency, and saving the cost required for the catalyst separation during the traditional batch reaction method.

4. It is easy to conduct the continuous quenching, liquid-liquid extraction and separation, where the quenching process is fast and safe; the liquid-liquid separation has satisfactory separation effect; and the liquid-liquid extraction has high efficiency. The separation yield is close to the reaction yield. The reaction process and the liquid-liquid extraction-separation process are continuously performed, which greatly enhances the process efficiency, and improves the purity of the final product diclofenac sodium.

5. The production method provided herein enables the continuous flow synthesis from the raw material to the diclofenac sodium in the absence of external interventions, and has high automation degree, great time and space efficiency, reduced labor intensity and lowered production cost.

BRIEF DESCRIPTION OF THE DRAWINGS

This FIGURE schematically shows a structure of a continuous-flow reaction system according to an embodiment of this application.

DETAILED DESCRIPTION OF EMBODIMENTS

In order to clearly explain the technical solutions, structural features, objectives and advantages of the disclosure, the disclosure will be described in detail below with reference to the embodiments and accompanying drawings. It should be understood that the embodiments are merely illustrative, and are not intended to limit the scope of the application.

A continuous-flow reaction system used in the following embodiments is structurally shown in the FIGURE.

Unit A (amidation unit) includes an aniline pipeline 1, a chloroacetic acid pipeline 2, a first feed pump 3, a second feed pump 4, a first mixer 5, a first microchannel reactor 6, a first back pressure valve 7, a first inorganic base pipeline 8, a first organic solvent pipeline 9, a third feed pump 10, a fourth feed pump 11, a first liquid-liquid extraction separator 12, a water phase outlet pipeline 13, an organic phase outlet pipeline 14, a second organic solvent pipeline 15, a fifth feed pump 16, a first concentration device 17, a first solvent recovery pipeline 18, a first storage tank 19 and a sixth feed pump 20.

Unit B (condensation and Smiles rearrangement unit) includes the sixth feed pump 20, a 2-chloro-N-phenylacetamide pipeline 21, a second microchannel reactor 22, a 2,6-dichlorophenol pipeline 23, a second mixer 24, a seventh feed pump 25, a second back pressure valve 26, a third organic solvent pipeline 27, an eighth feed pump 28, a second concentration device 29, a second solvent recovery pipeline 30, a beating filter device 31, a fourth organic solvent pipeline 32, a ninth feed pump 33, a filtrate outlet pipeline 34, a third concentration device 35, a fifth organic solvent pipeline 36, a tenth feed pump 37, a third solvent recovery pipeline 38, a reaction material circulation pipeline 39, an eleventh feed pump 40, a N-(2,6-dichlorophenyl)-2-hydroxyl-N-phenylacetamide outlet pipeline 41, a second storage tank 42 and a twelfth feed pump 43.

Unit C (chlorination unit) includes the twelfth feed pump 43 and a thirteenth feed pump 44, a N-(2,6-dichlorophenyl)-2-hydroxyl-N-phenylacetamide pipeline 45, a thionyl chloride pipeline 46, a third mixer 47, a third microchannel reactor 48, a third back pressure valve 49, a first liquid-liquid extraction separator 50, a water phase pipeline 51, a fourteenth feed pump 52, a water phase outlet pipeline 53, a sixth organic solvent pipeline 54, a fifteenth feed pump 55, a fourth concentration device 56, a fourth solvent recovery pipeline 57, a third storage tank 58 and a sixteenth feed pump 59.

Unit D (Friedel-Crafts alkylation unit) includes the sixteenth feed pump 59 and a seventeenth feed pump 60, a N-(2,6-dichlorophenyl)-2-chloro-N-phenylacetamide pipeline 61, an aluminum chloride reaction liquid pipeline 62, a fourth mixer 63, a fourth microchannel reactor 64, a fourth back pressure valve 65, a second liquid-liquid extraction separator 66, a second inorganic base solution pipeline 67, a seventh organic solvent pipeline 68, an eighteenth feed pump 69 and a nineteenth feed pump 70, a water phase outlet pipeline 71, an eighth organic solvent pipeline 72, a twentieth feed pump 73, a fifth concentration device 74, a fifth solvent recovery pipeline 75, a fourth storage tank 76 and a twenty-first feed pump 77.

A unit E (hydrolysis unit) includes the twenty-first feed pump 77, a twenty-second feed pump 78, a 1-(2,6-dichlorophenyl)-1,3-dihydro-2H-indol-2-one pipeline 79, a third inorganic base solution pipeline 80, a fifth mixer 81, a fifth microchannel reactor 82, a fifth back pressure valve 83, a sixth concentration device 84, a water pipeline 85, a twenty-third feed pump 86, a sixth solvent recovery pipeline 87, a buffer tank 88, a twenty-fourth feed pump 89, a crystallization device 90, a filtrate pipeline 91 and a diclofenac sodium outlet 92.

In the unit A, a first inlet of the first mixer 5 is connected to the first feed pump 3, a second inlet of the first mixer 5 is connected to the second feed pump 4, and an outlet of the first mixer 5 is connected to an inlet of the first microchannel reactor 6. An outlet of the first microchannel reactor 6 is connected to the first back pressure valve 7. An outlet of the first back pressure valve 7 is connected to a first inlet of the first liquid-liquid extraction separator 12. A second inlet of the first liquid-liquid extraction separator 12 is connected to the third feed pump 10, a third inlet of the first liquid-liquid extraction separator 12 is connected to the fourth feed pump 11, the water phase outlet pipeline 13 of the first liquid-liquid extraction separator 12 is connected to a water phase collecting device, and the organic phase outlet pipeline 14 is connected to a first inlet of the first concentration device, and a second inlet of the first concentration device 17 is connected to the fifth feed pump 16. An outlet of the first concentration device 17 is connected to an inlet of the first storage tank 19, and an outlet of the first storage tank 19 is connected to the sixth feed pump 20.

In the unit B, a first inlet of the second mixer 24 is connected to the sixth feed pump 20, a second inlet of the second mixer 24 is connected to the 2-chloro-N-phenylacetamide pipeline 21, and an outlet of the second mixer 24 is connected to an inlet of the seventh feed pump 25. An outlet of a first portion of the seventh feed pump 25 is connected to the second back pressure valve 26. An outlet of the back pressure valve 26 is connected to an inlet of a second portion of the seventh feed pump 25, a controllable inlet of the second portion of the microchannel reactor 25 is connected to the eleventh feed pump 40, and an outlet of the second portion of the seventh feed pump 25 is connected to a first inlet of the second concentration device 29. A second inlet of the second concentration device 29 is connected to the eighth feed pump 28, and an outlet of the second concentration device 29 is connected to a first inlet of the beating filter device 31. A second inlet of the beating filter device 31 is connected to the ninth feed pump 33. A filtrate outlet of the beating filter device 31 is connected to a first inlet of the third concentration device 35. A second inlet of the third concentration device 35 is connected to the tenth feed pump 37. An outlet of the third concentration device 35 is connected to the eleventh feed pump 40. An outlet of the beating filter device 31 is connected to an inlet of the second storage tank 42, and an outlet of the second storage tank 42 is connected to the twelfth feed pump 43.

In the unit C, a first inlet of the third mixer 47 is connected to the twelfth feed pump 43, a second inlet of the third mixer 47 is connected to the thirteenth feed pump 44, and an outlet of the third mixer 47 is connected to an inlet of the third microchannel reactor 48. An outlet of the third microchannel reactor 48 is connected to the third back pressure valve 49, and the third back pressure valve 49 is connected to a first inlet of the first liquid-liquid extraction separator 50. A second inlet of the first liquid-liquid extraction separator 50 is connected to the fourteenth feed pump 52, and an outlet of the first liquid-liquid extraction separator 50 is connected is connected to a first inlet of the fourth concentration device 56. A second inlet of the fourth concentration device 56 is connected to the fifteenth feed pump 55, and an outlet of the fourth concentration device 56 is connected to an inlet of the third storage tank 58. An inlet of the third storage tank 58 is connected to the sixteenth feed pump 59.

In the unit D, a first inlet of the fourth mixer 63 is connected to the sixteenth feed pump 59, a second inlet of the fourth mixer 63 is connected to the seventeenth feed pump 60, and an outlet of the fourth mixer 63 is connected to an inlet of the fourth microchannel reactor 64. The back pressure valve 65 is connected to a first inlet of the second liquid-liquid extraction separator 66. A second inlet of the second liquid-liquid extraction separator 66 is connected to the eighteenth feed pump 69, a third inlet of the second liquid-liquid extraction separator 66 is connected to the nineteenth feed pump 70, and an outlet of the second liquid-liquid extraction separator 66 is connected to a first inlet of the fifth concentration device 74. A second inlet of the fifth concentration device 74 is connected to the twentieth feed pump 73. An outlet of the fifth concentration device 74 is connected to an inlet of the fourth storage tank 76. An outlet of the fourth storage tank 76 is connected to the twenty-first feed pump 77.

In the unit E, a first inlet of the fifth mixer 81 is connected to the twenty-first feed pump 77, and a second inlet of the fifth mixer 81 is connected to the twenty-second feed pump 78, an outlet of the fifth mixer 81 is connected to an inlet of the fifth microchannel reactor 82. An outlet of the fifth microchannel reactor 82 is connected to the fifth back pressure valve 83. The fifth back pressure valve 83 is connected to a first inlet of the sixth concentration device 84. The second inlet of the sixth concentration device 84 is connected to the twenty-third feed pump 86, and an outlet of the sixth concentration device 84 is connected to an inlet of the buffer tank 88. The outlet of the buffer tank 88 is connected to the twenty-fourth feed pump 89. The twenty-fourth feed pump 89 is connected to an inlet of the crystallization device 90. The filtrate pipeline 91 of the crystallization device 90 is connected to a filtrate collecting device, and a diclofenac sodium outlet 92 is configured to output a diclofenac sodium crystal.

This application will be described in detail below with reference to the embodiments to make the objectives, technical solutions, and advantages of this application clearer.

Example 1

1. Amidation

A solution of chloroacetic acid and boric acid in toluene and a solution of aniline in toluene were simultaneously transported to a T-type micromixer by using feed pumps and mixed at 20° C. The reaction mixture is then allowed to enter a microchannel reactor for amidation reaction, where a total volume of the microchannel reactor was 50 mL, and a temperature of the microchannel reactor was 120° C.; the concentration of raw materials and the flow rate of the feed pumps were adjusted, such that a molar ratio of aniline to chloroacetic acid to boric acid was 1:1.2:0.001; and a back pressure of a back pressure valve was set to 0.5 MPa. After reacted for 20 min (namely, a residence time of the reaction mixture in the microchannel reactor was 20 min), the reaction mixture was discharged from an outlet of the back pressure valve.

The reaction mixture was then fed into a liquid-liquid extraction separator, and at the same time, a saturated aqueous sodium carbonate solution and ethyl acetate were fed into the liquid-liquid extraction separator respectively for quenching and extraction-separation. An organic phase was collected, and fed to a concentration device for concentration at 10 MPa and 50° C. to obtain a crude product of 2-chloro-N-phenylacetamide. The crude product was dissolved with acetonitrile, and then pumped into the first storage tank.

2. Condensation and Smiles Rearrangement Reaction

The acetonitrile solution of 2-chloro-N-phenylacetamide, and a solution of 2,6-dichlorophenol and polyethylene glycol 400 (PEG-400) in acetonitrile were simultaneously pumped into the T-type micromixer and mixed at 20° C., where the concentration of raw materials and the flow rate were adjusted such that a molar ratio of 2-chloro-N-phenylacetamide to 2,6-dichlorophenol to PEG-400 was 1:1:0.001. The reaction mixture was transported to a micro fixed-bed reactor filled with sodium carbonate particles, where the micro fixed-bed reactor had a length of 20 cm, an inner diameter of 2 cm, and a total volume of 20 mL. A first portion of the micro fixed-bed reactor had a volume of 10 mL, and was kept at 100° C.; a residence time of the reaction mixture in the first portion of the micro fixed-bed reactor was 10 min; and a back pressure of a back pressure valve was set to 0.5 MPa. A second portion of the micro fixed-bed reactor had a volume of 10 mL, and was kept at 70° C.; and a residence time of the reaction mixture in the second portion of the micro fixed-bed reactor was 10 min. After flowing out from the micro fixed-bed reactor, the reaction mixture entered a concentration device for concentration at 10 MPa and 40° C. to obtain a 2-(2,6-dichlorophenyl)-N-phenylacetamide and N-(2,6-dichlorophenyl)-2-hydroxyl-N-phenylacetamide mixture, which was dissolved with n-hexane, filtered with a beating filter device at 20° C. for 10 min to obtain a filtrate and a filter cake. The filtrate was returned to the concentration device for concentration at 10 MPa and 40° C. to obtain a concentrated product, that was, 2-(2,6 dichlorophenoxy)-N-phenylacetamide, which was dissolved with acetonitrile, transported to an inlet of the second portion of the micro fixed-bed reactor for Smiles rearrangement and filtered with the beating filter device. The filter cakes (namely N-(2,6-dichlorophenyl)-2-hydroxyl-N-phenylacetamide) were combined, dissolved with dichloromethane to obtain a N-(2,6-dichlorophenyl)-2-hydroxyl-N-phenylacetamide solution, which was transported to a second storage tank.

3. Chlorination

The N-(2,6-dichlorophenyl)-2-hydroxyl-N-phenylacetamide solution and a solution of thionyl chloride and triethylamine in dichloromethane were simultaneously pumped into a T-type micromixer, and mixed at 20° C., where the concentration of raw materials and the flow rate were adjusted such that a molar ratio of N-(2,6-dichlorophenyl)-2-hydroxyl-N-phenylacetamide to thionyl chloride to triethylamine was 1:2:0.1. After that, the reaction mixture was transported into a tubular microchannel reactor, and reacted at 50° C. for 10 min, where a back pressure of a back pressure valve was set to 0.2 MPa, and the tubular microchannel reactor had a volume of 20 mL. After flowing out from the tubular microchannel reactor, the reaction mixture entered a membrane extraction separator, and at the same time, water was pumped into the membrane extraction separator to quench the reaction. After continuous extraction and separation, an organic phase was collected, and fed to a concentration device for concentration at 10 MPa and 40° C. to obtain a crude product of N-(2,6-dichlorophenyl)-2-chloro-N-phenylacetamide, which was then dissolved with chlorobenzene, and transported to a third storage tank.

4. Friedel-Crafts Alkylation

The N-(2,6-dichlorophenyl)-2-chloro-N-phenylacetamide solution and a chlorobenzene solution of aluminum trichloride were simultaneously pumped into a T-type micromixer and mixed at 60° C., where the concentration of the raw materials and the flow rate were adjusted such that a molar ratio of N-(2,6-dichlorophenyl)-2-chloro-N-phenylacetamide to aluminum trichloride was 1:1.2. The reaction mixture was transported into a tubular microchannel reactor, and reacted at 150° C. for 10 min, where a back pressure of a back pressure valve was set to 0.5 MPa, and the tubular microchannel reactor had a volume of 20 mL. After flowing out of the tubular microchannel reactor, the reaction mixture entered a membrane extraction separator, and at the same time, a saturated sodium carbonate solution and ethyl acetate were pumped into the membrane extraction separator respectively for quenching and extraction-separation. An organic phase was collected and transported to a concentration device for concentration at 5 MPa and 50° C. to obtain the Friedel-Crafts alkylation product, that was, 1-(2,6-dichlorophenyl)-1,3-dihydro-2H-indol-2-one crude product, which was then dissolved with ethanol, and pumped into a fourth storage tank.

5. Hydrolysis Reaction

The 1-(2,6-dichlorophenyl)-1,3-dihydro-2H-indol-2-one solution, and a 30% sodium hydroxide aqueous solution were simultaneously transported into a T-type micromixer and mixed at 30° C., where the concentration of raw materials and the flow rate were adjusted such that a molar ratio of 1-(2,6-dichlorophenyl)-1,3-dihydro-2H-indol-2-one to sodium hydroxide was 1:5. The reaction mixture was transported into a tubular microchannel reactor and reacted at 50° C. for 10 min, where a back pressure a back pressure valve was set to 0.1 MPa, and the tubular microchannel reactor had a volume of 20 mL. After flowing from the tubular microchannel reactor, the reaction mixture entered a concentration device for concentration at 10 MPa and 50° C., and then dissolved with water, transported to a buffer tank, and pumped into a crystallization device, where a residence time of the reaction mixture in the crystallization device was 30 min. After crystallization, a filtrate was discharged, and a diclofenac sodium crystal was obtained. As confirmed by Liquid chromatography-Mass Spectrometry (LC-MS), the substrate aniline had a conversion rate of 99.9%, and the product diclofenac sodium (1) had a yield of 89%, and a purity of 98%.

Example 2

Example 2 was basically the same as Example 1, except that in this example, in the amidation process, a molar ratio of aniline to chloroacetic acid to boric acid was 1:1.1:0.005; a temperature of the microchannel reactor was 110° C.; a residence time of the reaction mixture in the microchannel reactor was 15 min, and a back pressure of the back pressure valve was set to 0.2 MPa; and the reaction was quenched with a saturated aqueous sodium carbonate solution. In this example, the substrate aniline had a conversion rate of 99.8%, and the product diclofenac sodium (1) had a yield of 88%, and a purity of 96% (analyzed by LC-MS).

Example 3

Example 3 was basically the same as Example 1, except that in this example, in the condensation and Smiles rearrangement process, the micro fixed-bed reactor was filled with sodium bicarbonate; the reaction in the first portion was performed at 80° C. for 10 min, and the reaction in the second portion was performed at 50° C. for 10 min. In this example, the product diclofenac sodium (1) had a yield of 90%, and a purity of 98% (analyzed by LC-MS).

Example 4

Example 4 was basically the same as the Example 1, except that in this example, in the chlorination process, a molar ratio of N-(2,6-dichlorophenyl)-2-hydroxyl-N-phenylacetamide to thionyl chloride to triethylamine was 1:1.5:0.01; the reaction mixture was transported into a tubular microchannel reactor for reacting at 60° C. for 8 min. In this example, the product diclofenac sodium (1) had a yield of 89%, and a purity of 99% (analyzed by LC-MS).

Example 5

Example 5 was basically the same as the Example 1, except that in this example, in the Friedel-Crafts alkylation process, the reaction solvent used herein is toluene; a molar ratio of N-(2,6-dichlorophenyl)-2-chloro-N-phenylacetamide to aluminum trichloride is 1:3; the reaction mixture was transported into a tubular microchannel reactor for reacting at 130° C. for 15 min. In this example, the product diclofenac sodium (1) had a yield of 83%, and a purity of 94% (analyzed by LC-MS).

Example 6

Example 6 was basically the same as the Example 1, except that in this example, in the hydrolysis process, the inorganic base solution used herein is saturated sodium carbonate solution; the reaction mixture was transported into a tubular microchannel reactor for reacting at 80° C. for 30 min under a back pressure of 0.5 MPa. In this example, the product diclofenac sodium (1) had a yield of 81%, and a purity of 93% (analyzed by LC-MS).

Example 7

Example 7 was basically the same as the Example 1, except that in this example, the extraction separators used herein are all annular centrifugal extraction separators. In this example, the product diclofenac sodium (1) had a yield of 90%, and a purity of 99% (analyzed by LC-MS).

Comparative Example 1

Comparative Example 1 adopts a traditional batch reactor to prepare diclofenac sodium, and the specific preparation method was performed as follows.

Aniline (2.325 g, 25 mmol), sodium bicarbonate (2.10 g, 25 mmol), anhydrous toluene (50 mL) were added to a reaction flask, to which chloroacetyl chloride (2.825 g, 25 mmol) was added dropwise under stirring. The reaction mixture was refluxed under heating for 2 h, and subjected to azeotropic distillation for 2 h. After the reaction was completed, the reaction mixture was cooled to room temperature, added with 2,6-dichlorophenol (4.00 g, 24.5 mmol), anhydrous potassium carbonate (6.4 g, 46.4 mmol) and polyethylene glycol (PEG) (250 µL) and refluxed under stirring for 24 h. The reaction mixture was slightly cooled, added with sodium hydroxide (1.20 g, 30 mmol) and refluxed under stirring for 10 h. After cooled to room temperature, the reaction mixture was added with water, stirred for 20 min, neutralized with concentrated hydrochloric acid and subjected to extraction with toluene. Organic phases were combined, and subjected to vacuum distillation, and vacuum drying to obtain white power 2,6-dichloro-diphenylamine. The 2,6-dichloro-diphenylamine (2.38 g, 10 mmol) and chloroacetyl chloride (1.356 g, 1.2 mmol) were placed in a dry reaction flask, and refluxed under stirring for 2.5 h. The excess chloroacetyl chloride was recovered under reduced pressure. After slightly cooled, the reaction mixture was added with anhydrous aluminum chloride (3.07 g, 23 mmol) and iron powder (20 mg) and stirred at 160° C. for 2.5 h. Immediately, the reaction mixture was poured into crushed ice and 1,2-dichloroethane followed by stirring at 50-55° C. for 1 h to allow phase separation. The organic phase was collected, and the aqueous phase was subjected to extraction with 1,2-dichloroethane. The organic phases were combined, washed with a saturated sodium bicarbonate solution and water in sequence to neutrality, distilled to recover the solvent, and cooled to room temperature to precipitate a crude product. The crude product was subjected to recrystallization with methanol, and decoloration with activated carbon to obtain white powder 1-(2,6-dichlorophenyl)-1,3-dihydro-2H-indol-2-one. The 1-(2,6-dichlorophenyl)-1,3-dihydro-2H-indol-2-one (2.78 g, 10 mmol), 30% sodium hydroxide solution (5.95 mL), benzyltriethylammonium chloride (TEBAC, 150 mg) and dimethylbenzene (50 mL) were placed in a reaction flask, refluxed under stirring for 10 h for azeotropic distillation. Then the reaction mixture was added with water, heated under stirring for 2 h, cooled to below 10° C. to precipitate white powder, and filtered to obtain crude product. The crude product was subjected to recrystallization with water and decoloration with activated carbon to obtain white crystalline powder as diclofenac sodium. More than 55 h were consumed, and the total yield was merely 64%.

Compared with the traditional batch reactor method, the method provided herein for continuously preparing diclofenac sodium via the micro-reaction system significantly shortens the reaction time, maximally suppresses the side reaction, thereby improving the yield of the diclofenac sodium. In addition, after reaction, the method provided herein does not require the separation of the catalyst from the reaction mixture, which facilitates the continuous synthesis and enhances the time and space efficiency.

It should be noted that the embodiments are merely illustrative, and are not intended to limit the scope of the application. It should be understood that any modifications or replacements made by those skilled in the art without departing from the spirit shall fall within the scope of the present application defined by the appended claims.

What is claimed is:

1. A method for preparing diclofenac sodium using a continuous-flow reaction system, the continuous-flow reaction system comprising a first unit, a second unit, a third unit, a fourth unit and a fifth unit successively connected in series; the first unit comprising a first mixer, a first microchannel reactor and a first storage tank connected in sequence; the second unit comprising a second mixer, a second microchannel reactor, a third microchannel reactor, a filter and a second storage tank; the third unit comprising a third mixer, a fourth microchannel reactor and a third storage tank connected in sequence; the fourth unit comprising a fourth mixer, a fifth microchannel reactor, and a fourth storage tank connected in sequence; the fifth unit comprising a fifth mixer and a sixth microchannel reactor; and the method comprising:

(S1) respectively feeding a mixed solution of chloroacetic acid and a first catalyst, and an organic solution of aniline to the first mixer for mixing to obtain a first mixture; and allowing the first mixture to flow out of the first mixer and enter the first microchannel reactor for amidation reaction;

(S2) subjecting a reaction mixture flowing out of the first microchannel reactor to continuous quenching, liquid-liquid extraction and separation to collect an organic phase;

(S3) concentrating the organic phase obtained in step (S2) to obtain 2-chloro-N-phenylacetamide (3) followed by dissolving with a first organic solvent to obtain a 2-chloro-N-phenylacetamide (3) solution; and transporting the 2-chloro-N-phenylacetamide (3) solution to the first storage tank;

(S4) respectively transporting the 2-chloro-N-phenylacetamide (3) solution in the first storage tank, and a mixed solution of 2,6-dichlorophenol and a phase transfer catalyst to the second mixer to for mixing to obtain a second mixture; and allowing the second mixture to flow out of the second mixer and enter the second microchannel reactor and the third microchannel reactor in sequence for continuous condensation and Smiles rearrangement; wherein the second microchannel reactor and the third microchannel reactor are both filled with a basic catalyst;

(S5) concentrating a reaction mixture flowing out of the third microchannel reactor followed by dissolving with a second organic solvent obtain a suspension; and transporting the suspension to the filter for filtration to collect a filtrate and a filter cake; wherein the filter cake is N-(2,6-dichlorophenyl)-2-hydroxyl-N-phenylacetamide (5);

(S6) concentrating the filtrate followed by dissolution with a third organic solvent and transportation to the third microchannel reactor for Smiles rearrangement to allow 2-(2,6 dichlorophenoxy)-N-phenylacetamide (4) in the filtrate to be converted into N-(2,6-dichlorophenyl)-2-hydroxyl-N-phenylacetamide (5); and repeating step (S5) to obtain another filter cake;

(S7) combining filter cakes followed by dissolving with a fourth organic solvent to obtain a N-(2,6-dichlorophenyl)-2-hydroxyl-N-phenylacetamide (5) solution; and transporting the N-(2,6-dichlorophenyl)-2-hydroxyl-N-phenylacetamide (5) solution to the second storage tank;

(S8) respectively transporting the N-(2,6-dichlorophenyl)-2-hydroxyl-N-phenylacetamide (5) solution in the second storage tank and a mixed solution of thionyl chloride and a second catalyst to the third mixer for mixing to obtain a third mixture; allowing the third mixture to flow out of the third mixer and enter the fourth microchannel reactor for chlorination;

(S9) subjecting a reaction mixture flowing out from the fourth microchannel reactor to continuous quenching, liquid-liquid extraction and separation to collect an organic phase;

(S10) concentrating the organic phase obtained in step (S9) followed by dissolution with a fifth organic solvent to obtain a N-(2,6-dichlorophenyl)-2-chloro-N-phenylacetamide (6) solution; transporting the N-(2,6-dichlorophenyl)-2-chloro-N-phenylacetamide (6) solution to the third storage tank;

(S11) respectively transporting the N-(2,6-dichlorophenyl)-2-chloro-N-phenylacetamide (6) solution and an organic solution of aluminum chloride to the fourth mixer for mixing and preheating to obtain a fourth mixture; allowing the fourth mixture to flow out of the fourth mixer and enter the fifth microchannel reactor for Friedel-Crafts alkylation;

(S12) subjecting a reaction mixture flowing out of the fifth microchannel reactor to continuous quenching, liquid-liquid extraction and separation to collect an organic phase;

(S13) concentrating the organic phase obtained in step (S12) followed by dissolving with a sixth organic solvent to obtain a 1-(2,6-dichlorophenyl)-1,3-dihydro-2H-indol-2-one (7) solution; transporting the 1-(2,6-dichlorophenyl)-1,3-dihydro-2H-indol-2-one (7) solution to the fourth storage tank;

(S14) respectively transporting the 1-(2,6-dichlorophenyl)-1,3-dihydro-2H-indol-2-one (7) solution in the fourth storage tank and a solution of an inorganic base to the fifth mixer for mixing to obtain a fifth mixture; and allowing the fifth mixture to flow out of the fifth mixer and enter the sixth microchannel reactor for hydrolysis to obtain the diclofenac sodium (1);

as shown in the following reaction scheme:

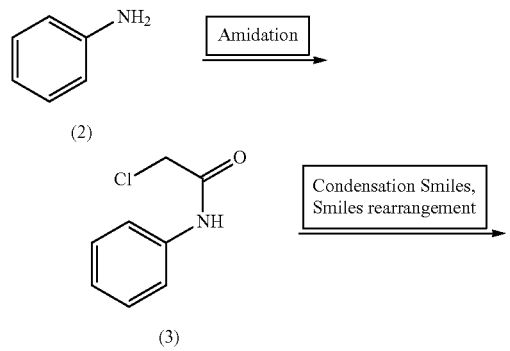

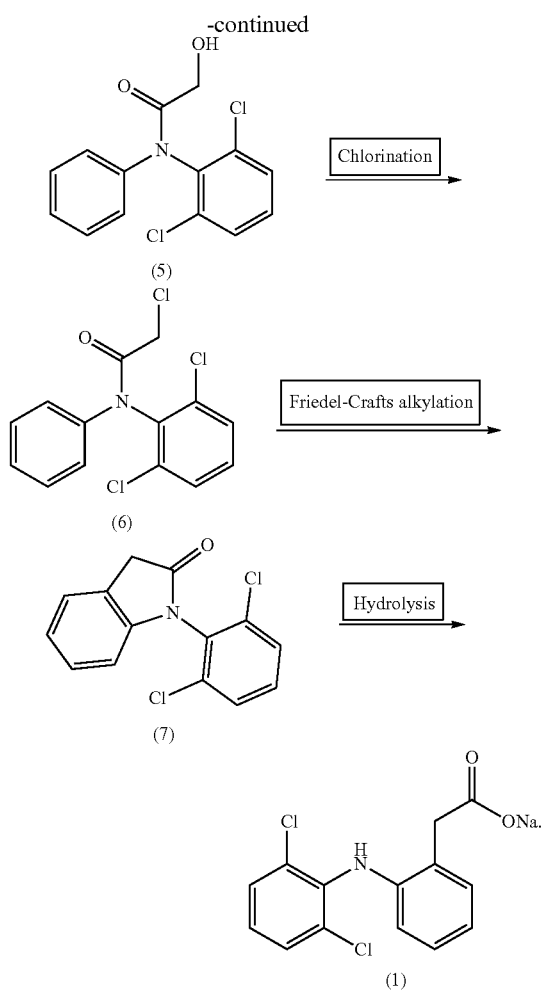

2. The method of claim 1, wherein in step (S1), the first catalyst is a boronic acid catalyst selected from the group consisting of o-halogenated arylboronic acid, aminoboronic acid, boric acid and boronate ester; a molar ratio of the aniline to the chloroacetic acid to the first catalyst is 1:(1-5):(0.001-0.5); the amidation reaction is performed in an organic solvent selected from the group consisting of toluene, xylene, mesitylene, chlorobenzene, dichlorobenzene, N,N-dimethylacetamide, ethyl acetate and acetonitrile; the first microchannel reactor is controlled at 70~170° C.; and a residence time of the reaction mixture in the first microchannel reactor is 5~100 min; and in step (S2), the reaction mixture flowing out from the first microchannel reactor is subjected to quenching with an aqueous solution of an inorganic base, liquid-liquid extraction with a non-polar organic solvent, and separation to collect the organic phase; the aqueous solution of the inorganic base contains 1~50% by weight of the inorganic base; the inorganic base is selected from the group consisting of sodium carbonate, potassium carbonate, sodium bicarbonate, potassium bicarbonate, sodium hydroxide and potassium hydroxide; a pH of the reaction mixture after quenched is 6-8; the non-polar organic solvent is an acetate solvent, a substituted benzene solvent or a halogenated hydrocarbon solvent; the liquid-liquid extraction is performed at 10-60° C.; the continuous quenching, liquid-liquid extraction and separation are performed in a first liquid-liquid extraction separator; a residence time of the reaction mixture in the first liquid-liquid extraction separator is 0.1-20 min; and in step (S3), the first organic solvent is selected from the group consisting of toluene, xylene, acetonitrile, N,N-dimethylformamide, ethyl acetate, acetone and n-butanol.

3. The method of claim 2, wherein in step (S4), the phase transfer catalyst is selected from the group consisting of polyethylene glycol 400 (PEG-400), polyethylene glycol 600 (PEG-600), benzyltriethylammonium chloride and tetrabutylammonium bromide; a molar ratio of the 2-chloro-N-phenylacetamide (3) to the 2,6-dichlorophenol to the phase transfer catalyst is 1:(0.5-2):(1-5); the basic catalyst is an inorganic base or an organic base; wherein the inorganic base is selected from the group consisting of sodium hydroxide, calcium hydroxide, sodium carbonate, sodium bicarbonate, potassium carbonate, potassium bicarbonate and sodium hydrogen; and the organic base is selected from the group consisting of a polymer-supported 1,8-diazabicyclo[5.4.0]undec-7-ene and a polymer-supported 1,5,7-triazabicyclo[4.4.0]dec-5-ene; and in step (S4), the second microchannel reactor is controlled at 50-160° C., and the third microchannel reactor is controlled at 0-100° C.; a residence time of the reaction mixture in the second microchannel reactor is 1-120 min, and a residence time of the reaction mixture in the third microchannel reactor is 0.5-40 min; and a back pressure of the third microchannel reactor is 0.1-5 MPa.

4. The method of claim 3, wherein in step (S5), the second organic solvent is a straight-chain alkane solvent, a substituted benzene solvent, an alkyl ether solvent or a cycloalkane solvent; the dissolution is performed at 0-60° C.; and a residence time of the suspension in the filter is 0.1-30 min; and in step (S6), the third organic solvent is selected from the group consisting of toluene, xylene, acetonitrile, N,N-dimethylformamide, ethyl acetate, acetone and n-butanol.

5. The method of claim 4, wherein in step (S7), the fourth organic solvent is selected from the group consisting of N,N-dimethylformamide, dimethyl sulfoxide, thionyl chloride, toluene, acetonitrile, dichloromethane, 1,2-dichloroethane and ethyl acetate;

in step (S8), the second catalyst is an organic base catalyst selected from the group consisting of pyridine, N,N-dimethylaniline, triethylamine and N,N-dimethylformamide; and in step (S8), a molar ratio of the N-(2,6-dichlorophenyl)-2-hydroxyl-N-phenylacetamide to thionyl chloride to the second catalyst is 1:(1-4):(0.001-0.5); the fourth microchannel reactor is controlled at 20~100° C., and a residence time of the reaction mixture in the fourth microchannel reactor is 10~60 min.

6. The method of claim 5, wherein in step (S9), the reaction mixture flowing out from the fourth microchannel reactor is subjected to quenching with an aqueous solution of an inorganic base, liquid-liquid extraction with a non-polar organic solvent, and separation to collect the organic phase; the aqueous solution of the inorganic base contains 1~50% by weight of the inorganic base; the inorganic base is selected from the group consisting of sodium carbonate, potassium carbonate, sodium bicarbonate, potassium bicarbonate, sodium hydroxide and potassium hydroxide; a pH of the reaction mixture after quenched is 6-8; the non-polar organic solvent is an acetate solvent, a substituted benzene solvent or a halogenated hydrocarbon solvent; the liquid-liquid extraction is performed at 10-60° C.; the continuous quenching, liquid-liquid extraction and separation are performed in a second liquid-liquid extraction separator; a residence time of the reaction mixture in the second liquid-liquid extraction separator is 0.1~20 min;

in step (S10), the fifth organic solvent is selected from the group consisting of dichloromethane, 1,2-dichloroethane, chlorobenzene, toluene, xylene, dichlorobenzene, n-butanol and diphenyl ether; and in step (S11), a molar ratio of the N-(2,6-dichlorophenyl)-2-chloro-N-phenylacetamide (6) to the aluminum chloride is controlled to be 1:(0.5-5); the fourth mixer is controlled at 10-100° C., and the fifth microchannel reactor is controlled to be 50-200° C.; and a residence time of the reaction mixture in the fifth microchannel reactor is 0.1~40 min.

7. The method of claim 6, wherein in step (S12), the reaction mixture flowing out of the fifth microchannel reactor is subjected to quenching with an aqueous solution of an inorganic base, liquid-liquid extraction with a non-polar organic solvent, and separation to collect the organic phase; the aqueous solution of the inorganic base contains 1~50% by weight of the inorganic base; the inorganic base is selected from the group consisting of sodium carbonate, potassium carbonate, sodium bicarbonate, potassium bicarbonate, sodium hydroxide and potassium hydroxide; a pH of the reaction mixture after quenched is 6-8; the non-polar organic solvent is an acetate solvent, a substituted benzene solvent or a halogenated hydrocarbon solvent; the liquid-liquid extraction is performed at 10-60° C.; the continuous quenching, liquid-liquid extraction and separation are performed in a third liquid-liquid extraction separator; and a residence time of the reaction mixture in the third liquid-liquid extraction separator is 0.1~20 min;

in step (S13), the sixth organic solvent is selected from the group consisting of toluene, xylene, diphenyl ether, methanol and ethanol; in step (S14), the solution of the inorganic base contains 5-50% by weight of the inorganic base, and the inorganic base is selected from the group consisting of sodium carbonate, potassium carbonate, sodium bicarbonate and sodium hydroxide; and in step (S14), the sixth microchannel reactor is controlled at 10-130° C., and a residence time of the reaction mixture in the sixth microchannel reactor is 1-60 min.

8. The method of claim 1, wherein the first mixer, the second mixer, the third mixer, the fourth mixer and the fifth mixer are each independently selected from the group consisting of static mixer, T-type micromixer, Y-type micromixer, cross-type mixer, coaxial flow micromixer and flow-focusing micromixer.

9. The method of claim 1, wherein the first microchannel reactor is a tubular microchannel reactor or a plate-type microchannel reactor; wherein the tubular microchannel reactor has an inner diameter of 100 μm~50 mm; the plate-type microchannel reactor comprises a first heat exchange layer, a reaction layer and a second heat exchange layer arranged in sequence from top to bottom; the reaction layer is provided with a reaction fluid channel; a hydraulic diameter of the reaction fluid channel is 100 μm~50 mm; and the first microchannel reactor is an agitated microchannel reactor;

the second microchannel reactor and the third microchannel reactor are respectively a fixed bed micro reactor; the fixed bed micro reactor has an inner diameter of 100 μm~20 cm, and a length of 2~50 cm; and one or more fixed bed micro reactors are connected in series to form an operation unit; and the fourth microchannel reactor, the fifth microchannel reactor and the sixth microchannel reactor are each independently a tubular microchannel reactor or a plate-type microchannel reactor; wherein the tubular microchannel reactor has an inner diameter of 100 µm-50 mm; the plate-type microchannel reactor comprises a first heat exchange layer, a reaction layer and a second heat exchange layer arranged in sequence from top to bottom; the reaction layer is provided with a reaction fluid channel; and a hydraulic diameter of the reaction fluid channel is 100 µm-50 mm.

10. The method of claim 7, wherein the first liquid-liquid extraction separator, the second liquid-liquid extraction separator, and the third liquid-liquid extraction separator are each independently a plate-type microchannel extraction separator, a membrane extraction separator, or an annular centrifugal extraction separator; wherein the plate-type microchannel extraction separator has an inner diameter of 100 µm-10 mm, and comprises a mixing layer and a separation layer; the membrane extraction separator has a hydrophobic membrane with a pore size of 0.1~4 µm; the annular centrifugal extraction separator has a diameter of 10 cm~1 m; and one or more annular centrifugal extraction separators are connected in series to form an extraction-separation unit.

\* \* \* \* \*